US012655355B2

(12) United States Patent
Arich de Finetti et al.

(10) Patent No.: US 12,655,355 B2
(45) Date of Patent: Jun. 16, 2026

(54) CHAR HANDLING SECTION AND DEPOLYMERIZATION PROCESS ASSOCIATED THEREWITH

(71) Applicant: Basell Poliolefine Italia S.r.l., Milan (IT)

(72) Inventors: Nicolò Arich de Finetti, Ferrara (IT); Diego Brita, Ferrara (IT); Antonio Mazzucco, Ferrara (IT)

(73) Assignee: Basell Poliolefine Italia S.r.l., Milan (IT)

( * ) Notice: Subject to any disclaimer, the term of this patent is extended or adjusted under 35 U.S.C. 154(b) by 416 days.

(21) Appl. No.: 18/268,076

(22) PCT Filed: Dec. 21, 2021

(86) PCT No.: PCT/EP2021/086927
§ 371 (c)(1),
(2) Date: Jun. 16, 2023

(87) PCT Pub. No.: WO2022/136334
PCT Pub. Date: Jun. 30, 2022

(65) Prior Publication Data
US 2024/0059974 A1     Feb. 22, 2024

(30) Foreign Application Priority Data
Dec. 22, 2020    (EP) .................................... 20216344

(51) Int. Cl.
| | |
|---|---|
| *C10B 57/00* | (2006.01) |
| *C07C 4/22* | (2006.01) |
| *C10B 53/07* | (2006.01) |

(52) U.S. Cl.
CPC .............. *C10B 57/005* (2013.01); *C07C 4/22* (2013.01); *C10B 53/07* (2013.01); *C10G 2300/1003* (2013.01); *C10J 2300/094* (2013.01)

(58) Field of Classification Search
None
See application file for complete search history.

(56) References Cited

U.S. PATENT DOCUMENTS

| | | | |
|---|---|---|---|
| 5,608,136 A | | 3/1997 | Maezawa et al. |
| 5,917,102 A | | 6/1999 | Holighaus et al. |
| 10,494,572 B2 | | 12/2019 | Methling |
| 2012/0125064 A1* | | 5/2012 | Joseph ................... C10B 53/02 |
| | | | 366/147 |
| 2016/0040074 A1 | | 2/2016 | Methling |
| 2019/0275486 A1 | | 9/2019 | Peltekis et al. |
| 2020/0103107 A1 | | 4/2020 | Inskip |

(Continued)

FOREIGN PATENT DOCUMENTS

| | | |
|---|---|---|
| JP | S6215240 A | 1/1987 |
| JP | H10236801 A | 9/1998 |
| JP | 2000192050 A | 7/2000 |

(Continued)

OTHER PUBLICATIONS

The International Search Report and the Written Opinion for PCT/EP2021/086927 mailed Apr. 8, 2022.

*Primary Examiner* — Ali Z Fadhel

(57) ABSTRACT

A char handling section of a depolymerization plant for processing a char-containing liquid slurry generated during progressive depolymerization of plastic waste material.

12 Claims, 2 Drawing Sheets

(56)  References Cited

U.S. PATENT DOCUMENTS

2022/0372374  A1 *  11/2022  Mikuskiewicz ....... C10G 1/002

FOREIGN PATENT DOCUMENTS

| | | | |
|---|---|---|---|
| TW | 201229099 | A | 7/2012 |
| WO | 9802401 | A1 | 1/1998 |
| WO | 2004087619 | A2 | 10/2004 |
| WO | 2007047063 | A2 | 4/2007 |
| WO | 2020084522 | A1 | 4/2020 |

* cited by examiner

CHAR HANDLING SECTION AND DEPOLYMERIZATION PROCESS ASSOCIATED THEREWITH

FIELD OF THE INVENTION

In general, the present disclosure relates to the field of chemistry. More specifically, the present disclosure relates to polymer chemistry. In particular, the present disclosure relates to a process for the depolymerization of plastic waste material and an apparatus for handling the char generated from the depolymerization process.

BACKGROUND OF THE INVENTION

In an attempt to mitigate the impact of plastic waste material on the environment, plastic materials coming from domestic and industrial waste are recycled and, in part, reintroduced into the production cycle. In some instances, recycling of plastic waste material reduces the use of fossil hydrocarbon sources for producing plastic items.

However and in some instances, mechanical recycling of plastic materials produces substances with lower quality, is costly and burdensome, and is not applicable to waste when the plastic is mixed with different materials.

In some instances and as a consequence, some plastic waste is used as a source of thermal energy in plants such as incinerators or disposed in landfills.

As used herein, the term "thermocatalysis" refers to a process for converting plastic waste material to liquid fuel (pyrolytic product) by thermal and optionally catalytic degradation in the absence of oxygen. In some instances, the plastic waste is first melted within a stainless steel chamber under an inert purging gas, such as nitrogen. In a first thermal step this chamber heats the molten material to a gaseous state. In a next thermocatalytic step, the gaseous material is cracked, thereby forming hydrocarbon chains of varying lengths (or hot pyrolytic gases).

The resulting hot pyrolytic gases are then condensed in one or more condensers, thereby yielding a hydrocarbon distillate made from or containing straight and branched chain aliphatic, cyclic aliphatic, and aromatic hydrocarbons (pyrolytic oil).

In some instances and notwithstanding the use of catalyst, the depolymerization reaction generates a by-product of sticky carbonaceous substances, partially in the form carbon, non-organic material, and residue of the depolymerization catalyst. It is believed that the non-organic material is derived from the additives contained in the plastics. As used herein, the term "char" refers to the resulting composition made from or containing the sticky carbonaceous substances. Due to the sticky nature, the char adheres to the reactor walls and lowers heat transfer coefficient, thereby also lowering the process productivity and efficiency.

In some instances, industrial pyrolysis or thermocatalytic plants have two pyrolysis chambers (that is, a twin-chamber system), which work in parallel at an approximately equal rate. In some instances and when both chambers complete the pyrolysis of waste material in unison, the chambers are cooled before removing the char from the internal base of each chamber. In some instances, the chambers work in alternate mode, thereby permitting the operator to clean one chamber while the other chamber is operating. The alternate mode reduces the amount of plastic treated per unit of time.

SUMMARY OF THE INVENTION

In a general embodiment, the present disclosure provides a char handling section including a first jacketed chamber, provided with inlet conduit for feeding a char-containing slurry, a stirring system capable of operating at a temperature ranging from 350 to 570° C., and a conduit for withdrawing a gaseous effluent;

a first structure for withdrawing a concentrated slurry from the first jacketed chamber, conveying the concentrated slurry to a stripping chamber, removing a gaseous effluent, and producing a drained char, wherein the first structure is capable of maintaining the slurry in the same temperature range of first jacketed chamber and has a degassing system;

a stripping chamber (6d), for receiving the drained char and removing gaseous effluent stripped out from the char, which is equipped with a stirring system (6d-1), a char outlet, (6d-2) a gas inlet (6d-3) located in the bottom of the stripping chamber, and a gas outlet (6d-4);

a second structure for receiving the dry char of stripping chamber and conveying the dry char to a collecting chamber, wherein the second structure is capable of maintaining the char at a temperature ranging from 60 to 100° C.; and a collecting chamber for receiving the dry char, provided with a stirring system and an outlet for char disposal operated by a valve.

DETAILED DESCRIPTION OF THE INVENTION

Figure 1:
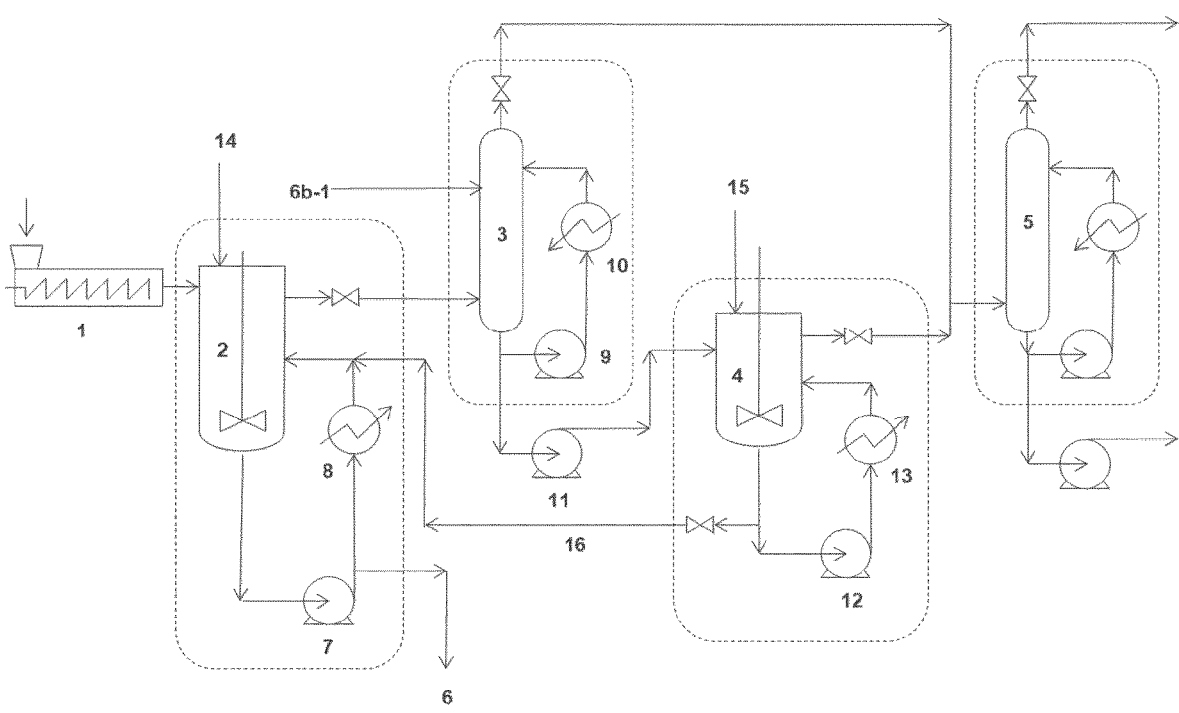
FIG. 1 shows a schematic of a thermocatalytic process plant.
Figure 2:
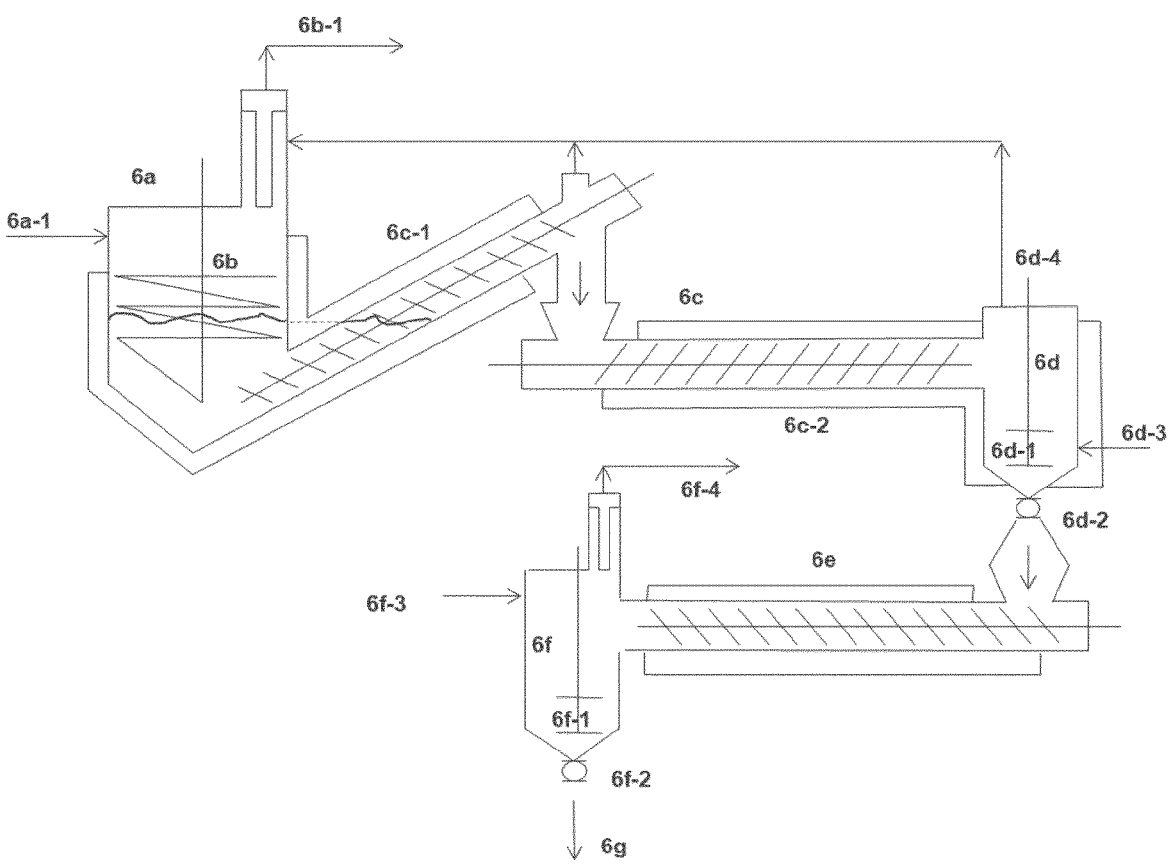
FIG. 2 shows a schematic of a char handling section.

In a general embodiment, the char handling section provides for isolating and disposing the solid portion of the slurry coming as effluent from a depolymerization reactor.

In some embodiments, the hot slurry withdrawn from a first depolymerization reactor (2) is sent to the jacketed chamber (6a) operating at a temperature ranging from 350 to 570° C. in which, by effect of the heat transferred by the hot jacket, depolymerization process takes place under stirring provided by the rotating blades (6b). In some embodiments, a gaseous effluent exits the chamber (6a), is sent to a first condensation unit (3), and is treated together with a first gaseous effluent of the first depolymerization reactor (2). In some embodiments, a filtering system is installed on the gas outlet conduit, for blocking entrained particles of char. In some embodiments, the gaseous effluent is first condensed in a dedicated unit and then sent back, by a pumping unit, to the first condensation unit (3).

In some embodiments, a concentrated slurry (mud) is formed and withdrawn from the bottom of chamber (6a) by a screw (hot) conveyor (6c) which transfers the concentrated slurry to a chamber (6d). In some embodiments, the screw conveyor (6c) is jacketed, thereby allowing the screw conveyor (6c) to operate at the same temperature range of chamber (6a). In some embodiments, molten solar salt is circulated within the jackets of chamber (6a) and screw conveyor (6c).

In some embodiments, the screw conveyor (6c) is made of two distinct conveyors connected to each other. In some embodiments, the concentrated slurry is withdrawn from the bottom of the first jacketed chamber (6a) by a first lifting screw conveyor (6c-1), having a lower end integrated with the bottom of first jacketed chamber (6a) and an upper end positioned at a higher height with respect to the lower end, and a second screw conveyor (6c-2) connected at a first end to the upper end of the lifting screw conveyor (6c-1) and connected at a second end to the upper portion of the stripping chamber (6d) for feeding the stripping chamber (6d). In some embodiments, the concentrated slurry is in the form of a mud. In some embodiments, both conveyors are jacketed and work in the same temperature range of chamber (6a).

While being elevated from the bottom of chamber (6a) and transferred via the second conveyor to stripping chamber (6d) the mud becomes progressively drained due to partial flowing back of liquid into chamber (6a) and partial conversion into gaseous effluent that is removed.

In some embodiments, the stripping chamber (6d) is fed with a char material containing a limited amount of liquid, alternatively being partially dried.

In some embodiments and in the stripping chamber (6d), nitrogen is injected into the bottom of the stripping chamber, thereby removing volatile hydrocarbon products. In some embodiments, the second structure (6e) is a jacketed screw conveyor. From the top of the stripping chamber (6d), the gases are withdrawn and sent to the first condensation unit (3) while, from the bottom of the chamber, the dry char is discharged into a jacketed screw conveyor (6e) maintained at a temperature ranging from 60 to 100° C., which conveys the char directly into a stirred collecting chamber (6f). In some embodiments, the dry char is discharged via a ball valve. In some embodiments, the stirred collecting chamber (6f) operates at about atmospheric pressure and a temperature ranging from 60 and 100° C. In some embodiments and in the collecting chamber, a nitrogen circulation is maintained via a gas inlet (6f-3) and a gas outlet (6f-4). The finally dry char is discharged via the valve (6f-2). The finally dry char is discharged into a mobile container (6g) and then disposed.

In some embodiments, the process is operated in a continuous mode without stopping depolymerization in the first depolymerization reactor (2). In some embodiments, a lighter depolymerization plant set up is provided. In some embodiments, the char handling section is fed with a slurry. In some embodiments, the char content in the slurry ranges from 10 to 50% wt; alternatively from 20 to 40% wt.

In some embodiments, the chair handling process releases a dried char made from or containing about 20% wt exhausted catalyst, 50% wt inorganics, and about 30% wt carbon, based upon the total weight of the char.

In some embodiments, the char handling section is associated to a depolymerization plant, operating a depolymerization reactor from which a liquid slurry containing the char is withdrawn.

In some embodiments, a process for depolymerizing waste plastic material and producing a pyrolytic product, includes the steps of:

(a) feeding a mixture made from or containing waste plastic material, in an oxygen-free atmosphere, into a feeding system including a screw extruder (1), heated to the melting temperature of the plastic material, and melting the plastic material, thereby forming a molten plastic material;

(b) removing the molten plastic material from the screw extruder (1) and feeding the molten plastic material into a first depolymerization reactor (2), being a continuously stirred tank reactor maintained at a temperature ranging from 280 to 600° C. and operated under a pressure ranging from 1 to 10 barg, thereby depolymerizing the plastic material and forming a first gaseous effluent and a first liquid effluent;

(c) directing a portion of the first liquid effluent to a char handling section (6) and feeding the first gaseous effluent to a first condensation unit (3) having a first operating temperature, thereby generating a gaseous stream and a liquid stream;

(d) directing the gaseous stream to a second condensation unit (5), having a second operating temperature lower than the first operating temperature of the first condensation unit (3) and directing the liquid stream to a second depolymerization reactor (4), being a continuously stirred tank reactor maintained at a temperature ranging from 280 to 600° C. and operated under a pressure ranging from 1 to 10 barg, thereby depolymerizing residual polymers from the first depolymerization reactor (2) and forming a second gaseous effluent and a second liquid effluent;

(e) withdrawing the second gaseous effluent from the second depolymerization reactor (4) and feeding the second gaseous effluent to the second condensation unit (5) and recycling a portion of the second liquid effluent to the first depolymerization reactor (2);

(f) recovering the pyrolytic product from the second condensation unit (5), wherein the first depolymerization reactor (2), the second depolymerization reactor (4), or both depolymerization reactors (2 and 4) operate in the presence of a depolymerization catalyst.

In some embodiments, the process is carried out in a continuous mode.

In stage (a), a charging system allows charging waste plastic materials to be fed into the first depolymerization reactor (2). In some embodiments, the charging occurs in continuous mode. In some embodiments, care is taken for not introducing oxygen containing atmosphere into the system. In some embodiments, the barrier to the potentially oxygen-containing atmosphere is obtained by nitrogen blanketing or a vacuum system connected to a barrel of the extruder.

In some embodiments, the plastic waste mixture is charged into the feeding system of the first depolymerization reactor (2) by a hopper or two or more hoppers in parallel. In some embodiments, the oxygen present in the atmosphere of the plastic waste material is eliminated inside the hopper(s).

In some embodiments, the plastic waste mixture is made from or containing a heterogeneous mixture of waste plastic materials, wherein the greater portion of the waste plastics materials are polyolefins. In some embodiments and in Italy, the heterogeneous mixture is referred to as Plasmix. In some embodiments, the pyrolytic product is recirculated back to a cracking/refining unit, wherein the plastic waste mixture is made from or containing polyolefin (PE and PP) content in an amount equal to or higher than 70% wt, based upon the total weight of the plastic waste mixture.

In some embodiments, the waste plastic material undergoes a pre-treatment stage, wherein the plastic material is melted by heat. In some embodiments, the waste plastic material undergoes a pre-treatment stage, wherein the waste plastic material is mixed with an additive. In some embodiments, the additive is an alkaline material. In some embodiments, the melting pretreatment transforms a non-uniform mixture of different kinds of waste plastics into a mass of uniform plastic composite. In some embodiments, the melting pretreatment occurs when the pyrolytic decomposition is performed without additives.

In some embodiments, the heating temperature in the pretreatment stage is set to a temperature based on the kind and content of the plastic contained in the waste plastic material such that pyrolytic decomposition of the plastic material to be treated is inhibited. In some embodiments, the temperature is within a range of 100° C. to 300° C., alternatively 150° C. to 250° C. In some embodiments, the waste plastic material is made from or containing PVC resin. In some embodiments, a temperature close to 300° C. or more eliminates HCl from PVC resin.

In some embodiments, the HCl forming gas is (a) removed via a venting system and successively neutralized or (b) trapped if the waste plastic material is mixed with an alkaline material during the melting/kneading pretreatment. In some embodiments, the melting operation uses kneaders or extruders with a screw. In some embodiments, the plastic waste is fed to the depolymerization reactor by an extruder.

In some embodiments, the extruder melts the plastic waste material, brings the plastic waste material to a temperature in the range of 250-350° C., and injects the molten plastic waste material into the first depolymerization reactor (2). In some embodiments, the extruder receives the plastic waste material cut in small pieces into the feed hopper, conveys the stream in the melting section, and heats the plastic waste material by combined action of mixing energy and heat supplied by barrel heaters.

In some embodiments, additives are incorporated in the melt, thereby reducing corrosivity of the plastic waste material or improving the conversion process in the reaction section.

In some embodiments and during the extrusion, one or more degassing steps remove residual humidity.

In some embodiments and before being fed to the first depolymerization reactor (2), the melt stream is filtered, thereby removing solid impurities.

In some embodiments, self-cleaning melt filters are operated for long time (several days) without manual intervention to replace filtration elements.

In some embodiments, the melt filter is based on a circular perforated plate as melt filtration element, holes by laser or by machining according to openings, where solid contaminant are accumulated. In some embodiments, an accumulation of impurities increases differential pressure across the melt filter. In some embodiments and for inline cleaning of the filtration element, a rotating scraper removes the accumulated impurities and guides the impurities to a discharge port. In some embodiments, the discharged port is opened for a period of time to purge contaminated material.

In some embodiments, this cycle is repeated several times (up to operation time of several days) without manual intervention or stopping production, to replace the filtration element.

In some embodiments, the self-cleaning melt filter is based on the application of continuous filtering metal bands through which polymer flows. In some embodiments, impurities are accumulated on the metal filter, thereby generating an increase of pressure. Accordingly, the clogged filtering band section is pushed out of the polymer passage area and a clean section is then inserted.

In some embodiments, this process is automatic, thereby allowing the process to operate for long time (up to several days) without manual intervention or stopping production to replace the filtration element.

In some embodiments, the extrusion systems are selected from the group consisting of single screw extruders, twin screw extruders, and twin screw extruders with gear pump.

In some embodiments and in step (b), the first depolymerization reactor (2) is an agitated vessel operated at a temperature ranging from 300 to 550° C., alternatively from 350 to 500° C.

In some embodiments, the operative pressure is in the range 2.0 to 8 barg, alternatively in the range 2.5 to 7 barg.

In some embodiments and for mass fluidity, the molten mass of waste plastics entering the reactor is pre-mixed with hydrocarbon oil, thereby promoting melt dissolution into the depolymerization reactor. In some embodiments, the pre-mixing occurs in a dedicated vessel. In some embodiments, the hydrocarbon oil is recirculated oil coming from the first condensation unit. In some embodiments, the volumetric ratio oil/molten mass ranges from 0.1:1 to 1:1.

In some embodiments, the first depolymerization reactor (2) has a cylindrical section. In some embodiments, the cylindrical section has a rounded bottom.

In some embodiments, the first depolymerization reactor (2) has a mixer installed in the vertical axis of the reactor, with a gear motor for rotating the blades of the mixer, thereby maintaining the system in stirred state. In some embodiments, the design of the mixer and the power of the motor vary in respect of the reactor content, volume, and shape. In some embodiments, the reactor operates with a power input ranging from 0.2 to 4 $kW/m^3$, alternatively 0.2-2 $kW/m^3$, alternatively from 0.3 to 1.5 $kW/m^3$.

In some embodiments, the thermal transfer induced by a flow of molten salt, heated to a temperature ranging from 300° C. to 570° C., heats the first depolymerization reactor.

In some embodiments, the feeding circuit (not shown) of the molten salt is constructed as to prevent molten salt leakage. In some embodiments, the molten salt is molten solar salt. In some embodiments, the molten salt is a mixture of sodium nitrate and potassium nitrate. In some embodiments, the sodium nitrate and potassium nitrate are present in a weight ratio ranging from 2:3 to 3:2. In some embodiments, the solar salt receives heat from a dedicated furnace. In some embodiments, the furnace is electric or fed with fuel. In some embodiments, part of the recovered oil from the second condensation unit (5) is used to feed the furnace. In some embodiments, the heat is generated by combustion of gaseous or liquid hydrocarbons. In some embodiments, the heat is generated by combustion of gaseous hydrocarbons.

In some embodiments, the heat associated to molten salt is transferred to the depolymerization reactor by circulating the molten salt through a jacket which envelops the whole reactor or by feeding the molten salt to an external heat exchanger.

In some embodiments, the salt is circulated by a circulation pump. In some embodiments, a series of fins provides a homogeneous distribution of the flow of molten salts in the jacket and maximization of the thermal exchange coefficient.

The depolymerization process taking place within the reactor produces molecules having reduced chain length and low boiling point. This continuously running chain breakage mechanism produces molecules increasingly smaller. In some embodiments, the chain breakage mechanism occurs close to the reactor walls. At the operating temperature and pressure, part of the resulting molecules is gaseous.

In some embodiments, the resulting composition within the reactor is made from or containing a range of hydrocarbons from methane to heavier products, both saturated and olefinic, with linear or highly branched structures. In some embodiments, the resulting composition is made from or containing aromatic molecules or molecules having fused rings structures.

In some embodiments, a part of the resulting molecules is liquid at the operating conditions and contributes to lowering the liquid mass viscosity. In some embodiments, the content of the first depolymerization reactor (2) is made from or containing a liquid slurry phase, wherein solid and inorganic substances are dispersed in a liquid hydrocarbon mixture, and a gaseous phase. In some embodiments, the solid substances are carbonaceous substances.

In some embodiments, part of the liquid slurry phase is withdrawn from the reactor and constitutes the first liquid effluent, which is sent to the char handling section (6). In some embodiments, the part of the liquid slurry phase is withdrawn from the bottom of the reactor.

In some embodiments, the withdrawal of the slurry phase from the bottom of the reactor is triggered by density sensors detecting the density of the liquid slurry reaching a predetermined value.

In some embodiments, part of the liquid slurry withdrawn from the first depolymerization reactor (2) is recirculated via a recycling pump (7) back to the reactor top optionally through an external heater (8). In some embodiments, heat to the external heater is provided by the molten salt.

In some embodiments, the liquid slurry portion recirculated to the reactor is withdrawn from a point of the reactor different from the point of the withdrawal of the liquid slurry portion sent to the char handling section (6).

In some embodiments, the liquid slurry portion recirculated to the reactor and the liquid slurry portion sent to the char handling section (6) are withdrawn from the same point and then successively split.

In some embodiments, the split between the portion of liquid slurry directed to the char handling section (6) and the portion recirculated to the reactor takes place before or after the recycling pump (7). In some embodiments, the liquid slurry is first fed to a dedicated vessel equipped with a lower exit point and an upper exit point. The liquid portion directed to the char handling section (6) is withdrawn in a concentrated form the lower exit point while the liquid portion to be recycled to the first depolymerization reactor (2) is withdrawn from the upper exit point.

The gaseous phase of the first depolymerization reactor (2) constitutes the first gaseous effluent, which is sent to the first condensation unit (3) for further treatment.

In some embodiments, the first gaseous effluent is made from or containing a mixture of light hydrocarbons. In some embodiments, the mixture of light hydrocarbons has heavy hydrocarbons and char particles entrained. In some embodiments, the first gaseous effluent is conveyed from the reactor top to a first condensation unit (3) operated at a pressure lower than the pressure of the first depolymerization reactor (2).

In some embodiments, the first condensation unit (3) is a scrubber column, thereby suppressing the entrained char. In some embodiments, the condenser temperature is selected such that the heavy hydrocarbons are condensed, and the light hydrocarbons are released as gaseous stream. The gaseous stream ($H_2$ and light hydrocarbons) is conveyed to the second condensation unit (5) working at a temperature lower than the first condensation unit (3) from which oil is recovered.

In some embodiments, the operative temperature of the first condensation unit (3) varies and depends on the operative pressure. In some embodiments and with atmospheric pressure, the operating temperature is from 20° C. to 200° C., alternatively from 50 to 200° C., alternatively from 60 to 180° C.

In some embodiments, the first condensation unit (3) is operated at about 80° C.

In some embodiments, the resulting liquid stream is made from or containing about 2 wt % or more of compounds with retention time equal to, or less than, n-heptane, about 25 wt % or more of compounds with retention time between n-heptane and n-dodecane, a larger fraction of compounds having a retention time higher than n-dodecane and lower than n-octacosane (70 wt % or less), and optionally a small amount of a fraction with higher retention time.

In some embodiments, a dephlegmator (partial condenser) is installed on top of the scrubber and works at a temperature lower than that inside the column. The condensate flows down as reflux for the scrubber by virtue of gravity. In some embodiments, the dephlegmator is installed as a separate piece of equipment or inside the scrubber.

In some embodiments, a pump recycles the liquid that collects in the bottom of the scrubber to the top of the column. The recycled liquid is cooled in a dedicated heat exchanger before injection into the scrubber top as reflux.

In some embodiments, the hydrocarbon condensate constitutes the liquid stream which is transferred by a pump to the second depolymerization reactor (4). In some embodiments, the hydrocarbon condensate has more than C7 carbon atoms.

In some embodiments, the second depolymerization reactor (4) is the same type as the first depolymerization reactor (2). In some embodiments, the second depolymerization reactor (4) is a continuously stirred tank reactor.

In some embodiments, the depolymerization takes place in the same range of temperatures. In some embodiments and to limit the volatility of the heavy hydrocarbons, the second depolymerization reactor (4) is operated at a pressure higher than the first depolymerization reactor (2), alternatively in the range from 2 to 10 barg, alternatively from 3 to 9 barg, alternatively from 3 to 8 barg.

It is believed that because the second depolymerization reactor (4) is fed with the condensed effluents coming from the first depolymerization reactor (2), the condensed effluent contains less impurities and produces less char. In some embodiments, fresh catalyst is fed to the second depolymerization reactor (4) through conduit (15).

In some embodiments, the catalyst is a depolymerization/cracking catalyst for thermocatalytic processes. In some embodiments, the catalyst is selected from the group consisting of metal oxides, heteropolyacids, mesoporous silica, and aluminosilicates catalysts. In some embodiments, the catalyst is selected from the group consisting of halloysite, kaolinite, and zeolites. In some embodiments, the zeolites are selected from the group consisting of synthetic Y-type zeolite and ZSM-5.

In some embodiments, the amount of catalyst feed is not more than 10% wt, alternatively not more than 5% wt, alternatively not more than 2% wt, with respect to the plastic waste feed.

In some embodiments, the catalyst is injected into the second reactor as powder dispersed into a hydrocarbon oil, alternatively the liquid pyrolytic product (oil) obtained from the first condensation unit (3) or the second condensation unit (5), alternatively the liquid pyrolytic product (oil) obtained from the first condensation unit (3).

In some embodiments, the catalyst slurry is prepared in a pot, being a continuously stirred vessel where the catalyst is poured from a dedicated silo to keep constant the concentration of the catalyst in the slurry.

In some embodiments, the pyrolytic oil dispersing the catalyst is withdrawn from the first condensation unit (3) to keep constant the slurry level in the pot. In some embodiments, the catalyst slurry is injected. In some embodiments, the catalyst slurry is injected into the second depolymerization reactor (4). In some embodiments, the catalyst slurry is injected by a progressive cavity pump, thereby maintaining the catalyst slurry's level constant.

In some embodiments, the second liquid effluent coming from the second depolymerization reactor (4) is a concentrated hydrocarbon slurry. In some embodiments, the second liquid effluent contains the depolymerization catalyst. In some embodiments, the second liquid effluent is discharged from the second depolymerization reactor (4) and sent back to the first depolymerization reactor (2) via the conduit (16). In some embodiments, the same density control in the second depolymerization reactor (4) for the withdrawal of the slurry is operated for the first depolymerization reactor (2).

In some embodiments, the slurry density is monitored by y-ray measurement or Coriolis densimeter. In some embodiments, the operative pressure of the first depolymerization reactor (2) is lower than the operating pressure of the second depolymerization reactor (4), thereby the light hydrocarbons of the slurry entering the first depolymerization reactor (2) vaporize and are extracted with the first gaseous effluent produced in the first depolymerization reactor (2).

In some embodiments, the amount of slurry recycled to the first depolymerization reactor (2) ranges from 5 to 40% in volume, alternatively from 10 to 30% in volume, of the second depolymerization reactor (4) content.

In some embodiments and in the second depolymerization reactor (4), part of the liquid slurry withdrawn from the bottom of the second depolymerization reactor (4) is recirculated, with a recycling pump (12), back to the top of the second depolymerization reactor (4) through an external heater (13).

The second gaseous effluent produced from the second depolymerization reactor (4) is conveyed to the second condensation unit (5) for recovering the pyrolytic product in the form of an oil.

In some embodiments, the second condensation unit (5) has a similar configuration to the first condensation unit (3).

In some embodiments, the second condensation unit (5) has a lower operating temperature and pressure than the first condensation unit (3).

In some embodiments, the operating temperature of the second condensation unit (5) ranges from 20 to 80° C., alternatively from 30 to 70° C. In some embodiments, the operating pressure value should of the second condensation unit (5) is lower than the operating pressure of the first condensation unit (3), thereby allowing incondensable gases from the first condensation unit (3) to enter the second condensation unit (5) without further pressurization. In some embodiments, the oil recovered from the second condensation unit (5) is lighter than the oil recovered from the first condensation unit (3). In some embodiments, the oil recovered from the second condensation unit (5) has the following composition (GC determined):

about 10-15% wt % of a fraction having a retention time equal or less than n-heptane, about 70-75 wt % of a fraction having a retention time between n-heptane and n-dodecane, about 12-20 wt % of a fraction having a retention time higher than n-dodecane and lower than n-octacosane, and no traces of compounds having a retention time higher than n-octacosane.

In some embodiments, the first liquid effluent discharged from the first depolymerization reactor (2) and directed to the char handling section (6) is in the form of slurry, which, being withdrawn from the lower part of the reactor, is concentrated. In some embodiments, the first liquid effluent is discharged continuously. It is believed that the pressure of a pressurized reactor permits the discharge of a concentrated slurry to a lower pressure device without using additional withdrawal equipment. In some embodiments, the slurry is discharged by the bottom of the reactor or from a line or vessel after the recycling pump (7).

In some embodiments, the flow of the slurry stream is continuous. In some embodiments, the char content in the slurry ranges from 10 to 50% wt, alternatively from 20 to 40% wt, based upon the total weight of the slurry.

What is claimed is:

1. A char handling section comprising:
   a first jacketed chamber, provided with inlet conduit for feeding a char-containing slurry, a stirring system, and a conduit for withdrawing of a gaseous effluent;
   a first structure for withdrawing a concentrated slurry from the first jacketed chamber and conveying the concentrated slurry to a stripping chamber, removing a gaseous effluent from the concentrated slurry, and producing a drained char from the concentrated slurry, wherein the first structure is capable of maintaining the slurry in the same temperature range of first jacketed chamber and has a degassing system;
   the stripping chamber for receiving the drained char and removing gaseous effluent stripped out from the char, which is equipped with stirring a system, a char outlet, a gas inlet located in the bottom of the stripping chamber, and a gas outlet;
   a second structure for receiving the dry char of stripping chamber and conveying the dry char to a collecting chamber, wherein the second structure is capable of maintaining the char at a temperature ranging from 60 to 100° C.; and
   a collecting chamber for receiving the dry char, provided with a stirring system and an outlet for char disposal operated by a valve.

2. The char handling section of claim 1, wherein the first jacketed chamber operates at a temperature ranging from 350 to 570° C.

3. The char handling section according to claim 1, wherein the first structure is a screw conveyor, which is jacketed and works at the same temperature range of the first jacketed chamber.

4. The char handling section according to claim 3, wherein molten solar salt is circulated within the jackets of the first jacketed chamber and the screw conveyor.

5. The char handling section according to claim 3, wherein the screw conveyor is made of two distinct conveyors connected to each other, the first conveyor being a lifting screw conveyor having a lower end integrated with the bottom of the first jacketed chamber and an upper end positioned at a higher height with respect to the lower end, and the second screw conveyor being connected at a first end to the upper end of the lifting screw conveyor and connected at a second end to the upper portion of the stripping chamber.

6. The char handling section according to claim 5, wherein both conveyors are jacketed and work at the same temperature range of first jacketed chamber.

7. The char handling section according to claim 1, wherein the stripping chamber is provided with a nitrogen inlet at the bottom of the stripping chamber and an outlet positioned at the top of the stripping chamber for conveying stripped gases to a condensation unit.

8. The char handling section according to claim 1, wherein the second structure is a jacketed screw conveyor and the bottom of the stripping chamber is provided with an outlet and a ball valve for discharging the dry char into the jacketed screw conveyor maintained at a temperature ranging from 60 to 100° C.

9. The char handling section according to claim 8, wherein the jacketed screw conveyor is connected to a collecting chamber having nitrogen circulation maintained via a gas inlet and a gas outlet.

10. The char handling section according to claim 1, being connected to a depolymerization plant comprising:

a feeding system of a mixture comprising waste plastic material, wherein the feeding system comprises a screw extruder, heated to the melting temperature of the plastic material, for melting the plastic material to form a molten plastic material, removing the molten plastic material from the screw extruder, and feeding the molten plastic material into a first depolymerization reactor;

the first depolymerization reactor, being a continuously stirred tank reactor maintained at a temperature ranging from 280 to 600° C. and operated under a pressure ranging from 1 to 10 barg, thereby depolymerizing the plastic material and forming a first gaseous effluent and a first liquid effluent, and having a first outlet for directing a portion of the first liquid effluent to the char handling section and a second outlet for directing the first gaseous effluent to a first condensation unit;

the first condensation unit for receiving the first gaseous effluent and having (i) a first operating temperature for generating a first gaseous stream and a first liquid stream from the first gaseous effluent, thereby generating the gaseous stream and the liquid stream, (ii) a first outlet for directing the first gaseous stream to a second condensation unit, and (iii) a second outlet for directing the first liquid stream to a second depolymerization reactor (4);

the second depolymerization reactor, being a continuously stirred tank reactor maintained at a temperature ranging from 280 to 600° C. and operated under a pressure ranging from 1 to 10 barg, thereby depolymerizing residual polymers from the first depolymerization reactor and forming a second gaseous effluent and a second liquid effluent, and having a catalyst feeding line, a first outlet for directing a portion of the second liquid effluent to the first depolymerization reactor, and a second outlet for directing the second gaseous effluent to a second condensation unit (5); and the second condensation unit for receiving the first gaseous stream and the second gaseous effluent, having (i) a second operating temperature lower than the first operating temperature of the first condensation unit, thereby generating a second gaseous stream and a second liquid stream, (ii) a first outlet for recovering the second gaseous stream as a pyrolytic product, and (iii) a second outlet for recycling a portion of the second liquid stream to the second depolymerization reactor.

11. A process for handling a char-containing slurry comprising the steps of:

introducing a char-containing slurry into a first jacketed chamber, provided with a stirring system, and operating the first jacketed chamber at a temperature ranging from 350 to 570° C., thereby producing and withdrawing a gaseous effluent and concentrating the slurry and withdrawing the concentrated slurry from the first jacketed chamber and conveying the concentrated slurry to a stripping chamber while maintaining the slurry in the same temperature range of the first jacketed chamber and removing a gaseous effluent from the concentrated slurry, thereby producing a drained char from the concentrated slurry;

introducing the drained char into a stripping chamber, equipped with a stirring system, a char outlet, a gas inlet located in the bottom of the stripping chamber, and a gas outlet, thereby producing a dry char;

feeding the dry char to a collecting chamber while maintaining the char at a temperature ranging from 60 to 100° C.; and discharging the dry char from the collecting chamber via a valve and disposing of the dry char.

12. The process according to claim 11, wherein the char content of the slurry ranges from 10 to 50% wt, with respect to the total weight of the slurry.

* * * * *